US006904789B2

(12) United States Patent
Campbell et al.

(10) Patent No.: US 6,904,789 B2
(45) Date of Patent: Jun. 14, 2005

(54) MOISTURE DETECTION APPARATUS AND METHOD

(75) Inventors: Gaylon S. Campbell, Pullman, WA (US); Warren C. Greenway, Cambridge, ID (US)

(73) Assignee: Decagon Devices, Inc., Pullman, WA (US)

( * ) Notice: Subject to any disclaimer, the term of this patent is extended or adjusted under 35 U.S.C. 154(b) by 280 days.

(21) Appl. No.: 09/905,761

(22) Filed: Jul. 13, 2001

(65) Prior Publication Data

US 2003/0015024 A1 Jan. 23, 2003

(51) Int. Cl.[7] ................................................ G01N 5/02
(52) U.S. Cl. .................... 73/73; 73/73; 73/74; 73/75; 324/664
(58) Field of Search .............................. 73/73, 74, 75; 324/664; 137/78.3

(56) References Cited

U.S. PATENT DOCUMENTS

| | | | | |
|---|---|---|---|---|
| 3,771,548 A | * | 11/1973 | Rauchwerger | 73/304 C |
| 3,965,416 A | | 6/1976 | Friedman | 324/58.5 B |
| 3,968,428 A | * | 7/1976 | Numoto | 324/694 |
| 4,052,666 A | * | 10/1977 | Fletcher et al. | 324/631 |
| 4,177,434 A | * | 12/1979 | Ida | 73/54.26 |
| 4,341,112 A | * | 7/1982 | Mackay et al. | 73/73 |
| 4,389,900 A | | 6/1983 | Gutierrez | 73/861.42 |
| 4,646,000 A | * | 2/1987 | Wills | 324/674 |
| 5,136,249 A | | 8/1992 | White et al. | 324/643 |
| 5,148,125 A | | 9/1992 | Woodhead | 331/135 |
| 5,212,453 A | * | 5/1993 | Koehler et al. | 324/664 |
| 5,376,888 A | * | 12/1994 | Hook | 324/533 |
| 5,402,075 A | * | 3/1995 | Lu et al. | 324/664 |
| 5,424,649 A | | 6/1995 | Gluck et al. | 324/667 |
| 5,445,178 A | | 8/1995 | Feuer | 137/1 |
| 5,459,403 A | * | 10/1995 | Kohler et al. | 324/643 |
| 5,859,536 A | * | 1/1999 | Stockton | 239/64 |
| 5,969,620 A | * | 10/1999 | Okulov | 340/620 |
| 6,060,889 A | | 5/2000 | Hocker | 324/667 |
| 6,107,809 A | * | 8/2000 | Moshe et al. | 324/637 |
| 6,204,670 B1 | * | 3/2001 | Joshi | 324/636 |

FOREIGN PATENT DOCUMENTS

AT                403213 B   * 10/1997   .......... G01N/27/22

OTHER PUBLICATIONS

Article in *Computers and Electronics in Agriculture*, 1998, pp. 31–44, written by Gaylon S. Campbell and Russell Y. Anderson entitled "Evaluation of Simple Transmission Line Oscillators for Soil Moisture Measurement".

* cited by examiner

*Primary Examiner*—Hezron Williams
*Assistant Examiner*—André K. Jackson
(74) *Attorney, Agent, or Firm*—Holland & Hart

(57) ABSTRACT

A sensor to detect the presence of water or moisture in bulk materials includes a standard circuit board and a three element transmission line. The sensor electronics include an oscillator responsive to a direct current voltage supply which provides a square wave voltage signal. The sensor electronics further include a phase detector which detects the difference in phase between the reference square wave voltage signal and a signal provided to the transmission line buried in a medium. The phase difference is proportional to the dielectric constant of the medium surrounding the transmission line.

14 Claims, 4 Drawing Sheets

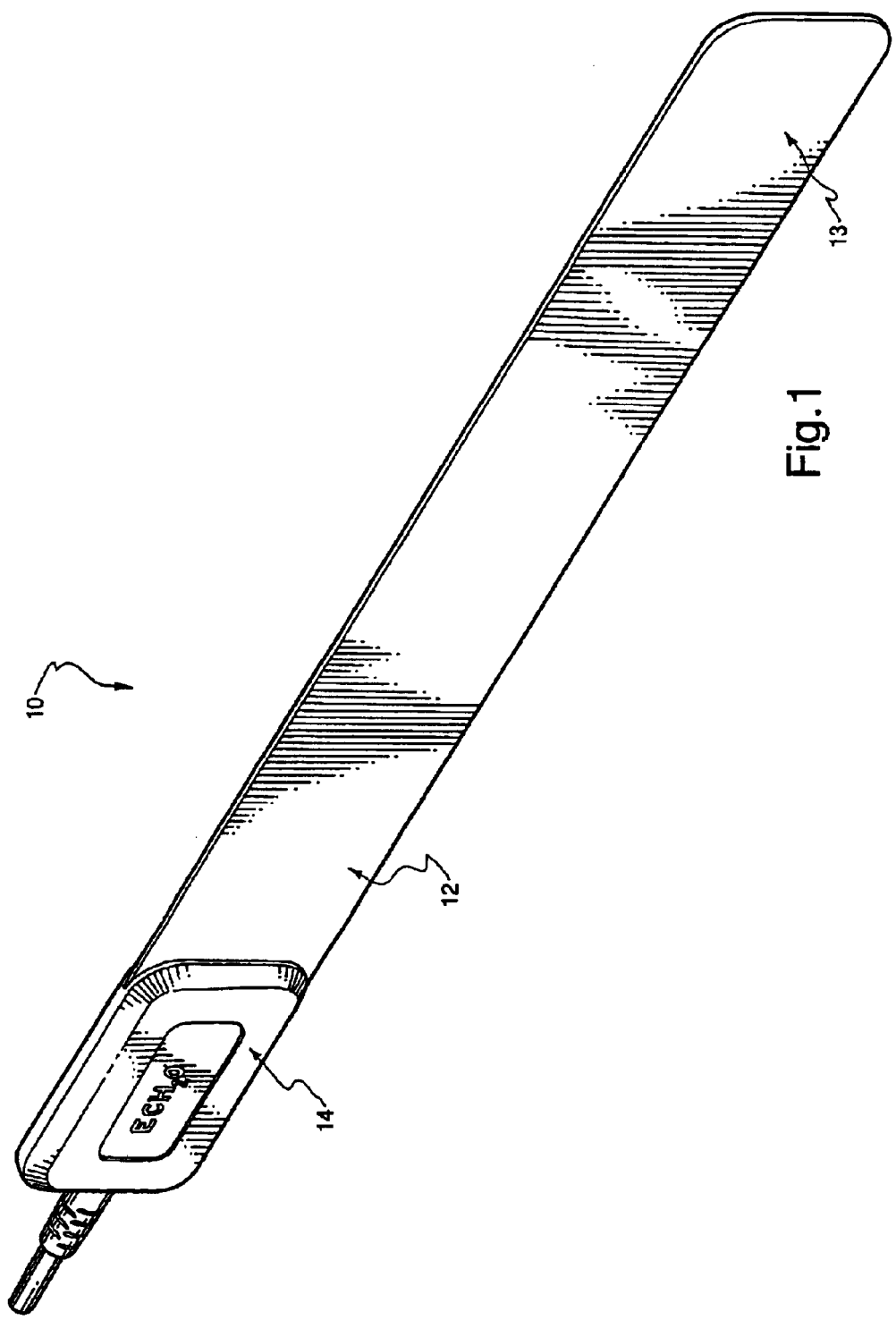

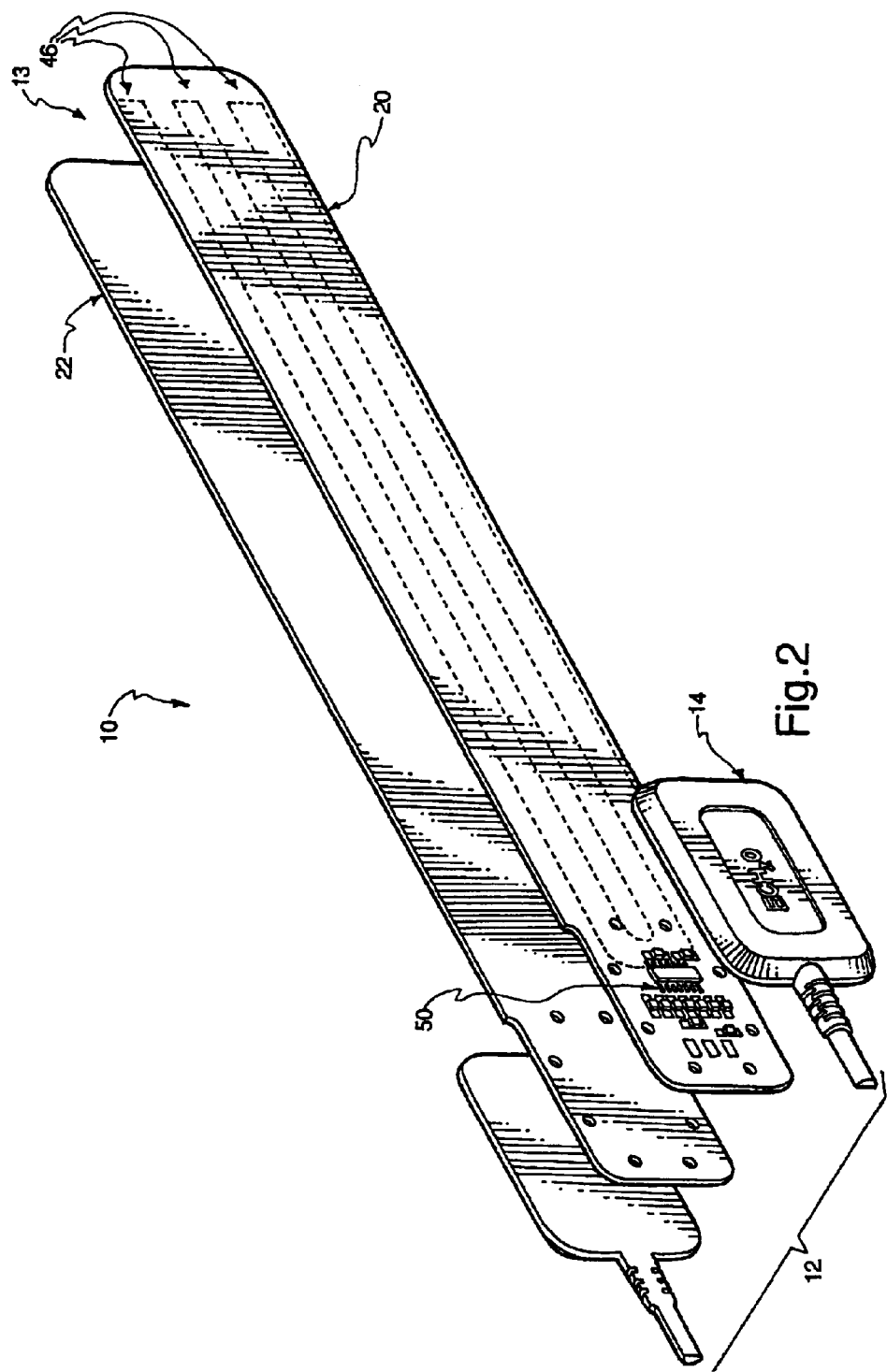

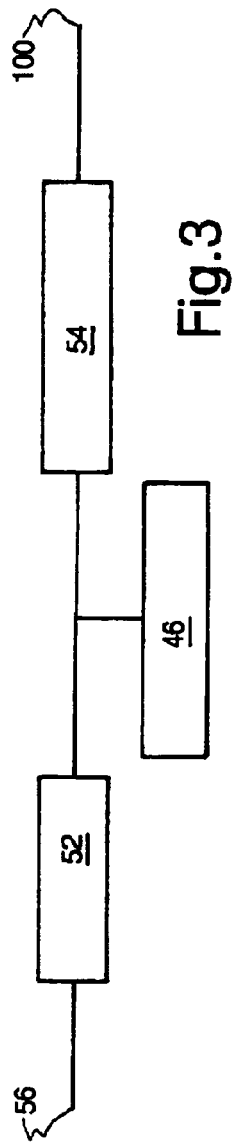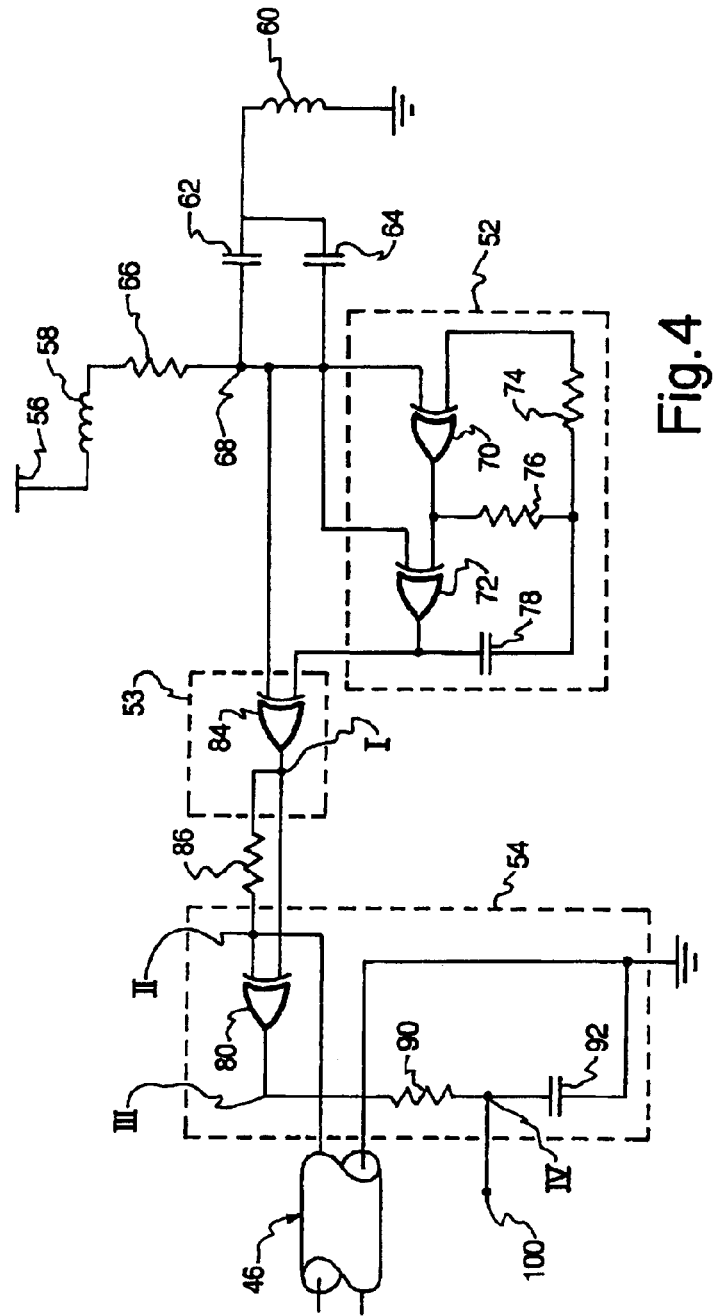

MOISTURE DETECTION APPARATUS AND METHOD

TECHNICAL FIELD

The present invention relates to a method and apparatus to detect the presence of moisture, and more particularly, to a method and apparatus to measure water content in bulk materials such as soils and food products, by measuring changes in the dielectric constant of the material.

BACKGROUND OF THE INVENTION

Several methods and devices have traditionally been used to measure the water or moisture content of bulk materials, such as soils and food products. One well-known technique is to measure changes in the dielectric constant of the medium being measured. The dielectric constant of water is approximately 80, the dielectric constant of soil minerals and organic matter is around 4, and the dielectric constant of air is 1. Accordingly, changes in water content of a particular medium will result in large changes in the dielectric constant of the medium, which can readily be measured.

There are numerous specific examples where knowing the moisture or water content can be critical. For example, without limitation, the moisture content of soil can give information which is useful for conserving applied irrigation water or reducing ground water contamination. Moisture content measurements on stored grain can be used to prevent spoilage.

A particular problem with measuring and monitoring moisture content of materials, particularly soils, has been the expense and sophisticated nature of the equipment used to measure or monitor the soil. Traditional devices for measuring moisture content in soils have been relatively large and very expensive to manufacture. Generally, many hundreds of dollars have traditionally been required to manufacture a single moisture measuring apparatus. This has traditionally made it cost prohibitive for those in agriculture, for example, to use multiple moisture content measuring devices in a field.

An explanation of use of a transmission line buried in soil to detect the presence of moisture in the soil by measuring the travel time of an electrical pulse in the transmission line is found in the publication entitled *Evaluation of simple Transmission Line Oscillators for Soil Moisture Measurement,* 20 COMPUTERS AND ELECTRONICS IN AGRICULTURE (1998), pp. 31–44, authored by Gaylon S. Campbell and Russell Y. Anderson, which is incorporated in its entirety by this reference.

Various other methods and apparatus exist for detecting the presence of moisture in porous materials. For example, many devices, such as that shown in U.S. Pat. No. 5,148,125, determine the presence of moisture in a material by measuring the propagation delay of an AC signal applied to a transmission line buried in the material. Systems such as these suffer from the disadvantage that, for operation, a user must have access to both ends of the transmission line.

In view of the foregoing, there is a need to provide a moisture detection apparatus and method which will be relatively inexpensive to manufacture, easy to use in the field, and provide accurate data concerning the moisture content of porous materials.

SUMMARY AND OBJECTS OF THE INVENTION

An object of the invention is to measure moisture content of bulk materials.

Another object of the invention is to utilize time domain reflectometry (TDR) to measure the moisture content of bulk materials.

Still another object of the invention is to utilize frequency domain methods (FD) to measure the moisture content of bulk materials.

Yet another object of the invention is to provide a device for measuring the moisture content of bulk materials which is inexpensive to manufacture.

Another object of the invention is to provide a device for measuring the moisture content of bulk materials which is easy to use in the field and can be readily installed at various locations.

Another object of the invention is to provide an apparatus and method for detecting moisture content which utilizes a constant frequency and measures a phase lag to determine the dielectric constant of the medium in which the water content is being measured.

Still another object of the invention is to utilize a single integrated circuit chip to produce oscillation, buffer a signal, and detect the phase while producing a voltage output.

Another object of the invention is to use a circuit board both to route signals and secure circuit components, as well as to form the elements of the moisture sensor.

The foregoing objects are achieved by the present invention which provides a sensor for detecting the presence of water or moisture in bulk materials. The sensor comprises, in one embodiment, a standard four-layer printed circuit board assembly consisting of two printed circuit boards bonded together. The circuit is etched in the top layer of the top board and a three element transmission line is etched in the second layer of the same board. A second P.C. board, identical in size and thickness to the first, but with no copper cladding, is bonded to the bottom side of the first board so the transmission line is insulated from the medium in which it is placed. An overmold seals and protects the circuit components, which are mounted on one end of the board on the top layer.

The sensor electronics of the subject invention include an oscillator that is responsive to a direct current voltage supply for providing a square wave voltage signal. The sensor electronics also include the above-mentioned transmission line. The transmission line input is coupled to receive the square wave voltage signal. A phase detector is coupled to detect the difference in phase between a reference square wave voltage signal and the signal provided to the transmission line. The phase difference is proportional to the dielectric constant of the medium surrounding the transmission line.

Other objects, features, and advantages of the invention will become apparent from the following detailed description of the invention with reference to the accompanying drawings.

BRIEF DESCRIPTION OF THE DRAWINGS

Preferred embodiments of the invention are described below with reference to the accompanying drawings:

FIG. 1 is a perspective view of a moisture sensor according to the present invention;

FIG. 2 is an exploded perspective view of the moisture sensor of FIG. 1;

FIG. 3 is a block diagram of the moisture sensor electronics;

FIG. 4 is a schematic diagram of the essential electronic components utilized in connection with the present invention.

DETAILED DESCRIPTION OF THE INVENTION

Figure 5:
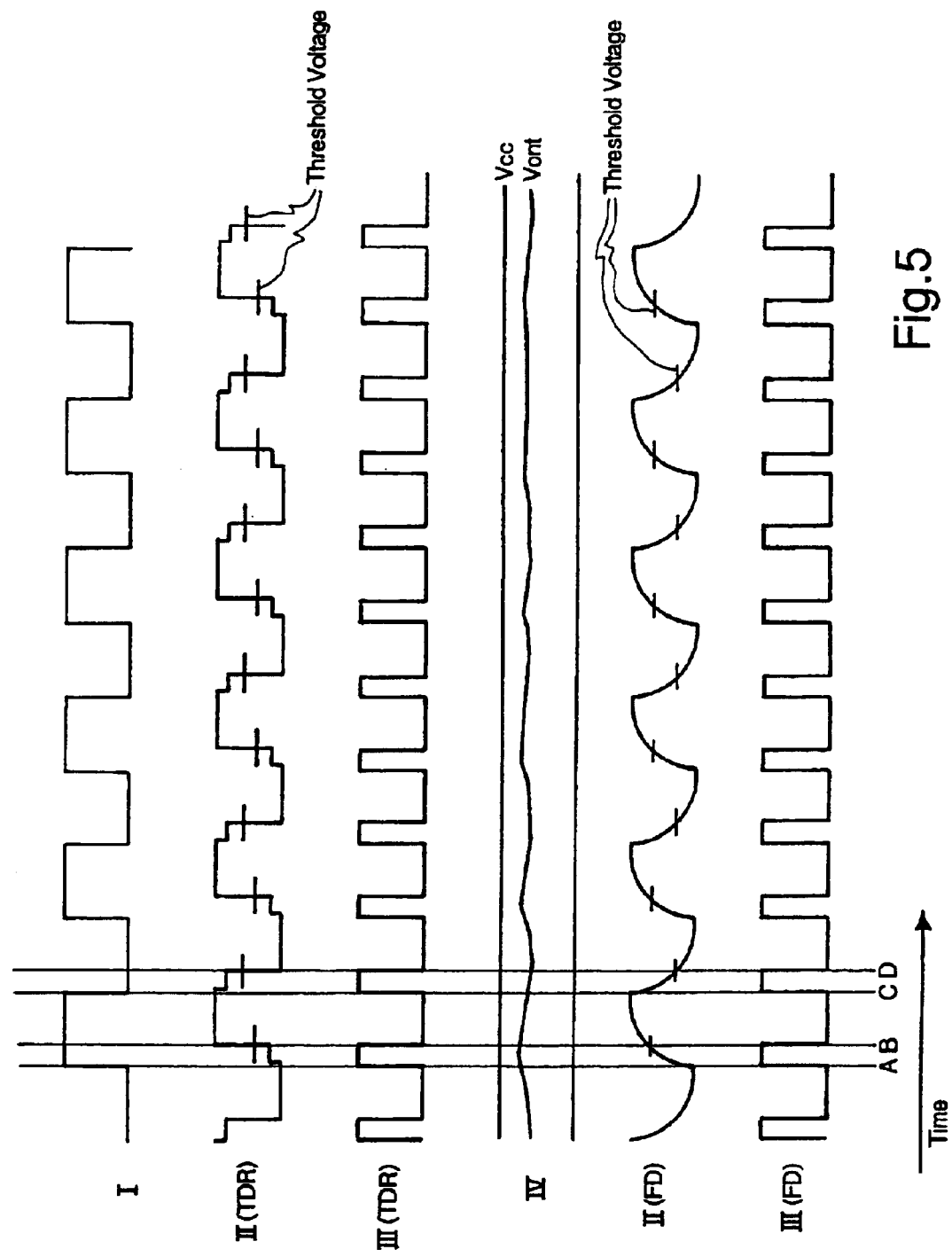
FIG. 5 is a diagram showing various output voltages utilized and measured in connection with the present invention.

The present invention comprises an improved moisture sensor 10, illustrated in FIGS. 1 and 2. The moisture sensor 10 generally comprises a four layer printed circuit board 12, that is shaped as a thin, flat probe to facilitate its use in probing materials. An overmolded plastic enclosure forms an electronics compartment or housing 14. The electronics compartment 14 is constructed for housing electronic components as will be discussed more fully below. The moisture sensing apparatus 10 further includes a distal end 13 which forms a transmission line sensor. The transmission line is insulated from the medium by the non-conducting P.C. board material, reducing errors in high salinity environments.

FIG. 2 shows an exploded perspective view of the sensor 10. Moisture sensor 10 comprises first and second P.C. board layers 20 and 22, each having a similar size and shape so that they can mate with and be bonded to one another. A three element transmission line 46, is etched in the copper of the underside of the first layer 20, and is insulated from the measurement medium on the upper side by board 20 and on the lower side by board 22.

Sensor electronics 50 are preferably mounted on the top of the circuit board, which forms part of the first layer 20.

It should be understood that in a preferred embodiment FR 4 type material may be used for each of the layers 20 and 22. FR 4 comprises typical circuit board material comprising a composite fiberglass and epoxy material. An epoxy paint may be utilized to coat the outer layers of 20 and 22. Other suitable materials may also be used.

An illustrative block diagram of the semiconductor circuit showing the sensor electronics 50 is provided in FIG. 3. Therein, the sensor electronics 50 includes an oscillator 52 for providing a square wave voltage signal. The oscillator 52 is coupled to the transmission line 46 for providing the square wave voltage signal thereto. A phase detector 54 is coupled to the oscillator 52 and the transmission line 46 to detect the difference in phase between the reference square wave voltage signal and the signal provided to the transmission line. The details of components included in each of these three blocks are show in FIG. 4, along with a buffer block 53 which buffers the square wave signal from the oscillator to the transmission line.

More particularly, as shown in FIG. 4, a suitable source voltage is provided by a voltage 56, which is conditioned using first and second inductors 58, 60, respectively, first and second capacitors 62, 64, respectively, and a resistor 66, to provide the source voltage at node 68 and at the power supply pin of the I.C. (not shown). As shown, oscillator 52 comprises first and second exclusive OR gates 70, 72, respectively, which are configured as simple inverters, and with resistors 74, 76 and capacitor 78, form an astable multivibrator.

Configured as described, and with the proper selection of resistors 74, 76 and capacitor 78, oscillator 52 will provide an output that is the square wave voltage signal having a desired frequency. Buffer 53 is a single exclusive OR gate 84, configured as an inverter, which provides the square save signal from the oscillator 52 to the transmission line 46 and the phase detector 54.

Phase detector 54 has first and second inputs, which are operatively coupled to exclusive OR gate 80. The output of the buffer 53 is a square wave voltage signal and is provided directly to the first input of the phase detector 54. The second input of the phase detector 54 is coupled to the output of the buffer 53 through a third resistor 86. The second input of phase detector 54 is also coupled to the transmission line 46.

The output of the exclusive OR gate 80 is coupled to resistor 90 and capacitor 92 which form a low-pass filter giving an output voltage 100 that is constant and proportional to the difference in phase between the inputs of the phase detector. The four exclusive OR gates shown in FIG. 4 are commonly available in a single I.C. such as the 74VHC86.

FIG. 5 shows various example wave forms associated with the present invention. Reference numerals I through IV as shown in FIG. 5 correspond to those same reference numerals I through IV identified in FIG. 4. There are two wave forms shown at locations II and III, one for time domain reflectometry (TDR) and one for frequency domain (FD). The circuit will operate in either mode depending on the length of the transmission line and the speed of the exclusive OR gates 70, 72, 80, 84.

The voltage at I (FIG. 4) is a simple square wave, which is shown as wave I in FIG. 5. Wave I is the bottom input to the exclusive OR gate 80 (FIG. 4), while the top input to exclusive OR gate 80 is also operatively coupled to the moisture probe 46. The wave form II will behave differently depending on the length of the probe. For a long probe (e.g., a ten-foot probe), the circuit will operate in a TDR mode where the wave at II will show a low plateau when the leading edge of the square wave reaches the start of probe 46, and a peak plateau when it has reached the end of the probe and is reflected back to the start 46. For a short probe (e.g., a six-inch probe), the probe 46 will be in a FD mode, and the voltage at II will act like a charging and discharging capacitor (II FD in FIG. 5).

TABLE 1

Truth Table for Exclusive OR Gate 80

| X | Y | Output |
| --- | --- | --- |
| 0 | 0 | 0 |
| 0 | 1 | 1 |
| 1 | 0 | 1 |
| 1 | 1 | 0 |

Considering a long probe 46, operating in a TDR mode when the wave I changes from low to high (at time A), wave I will be high while wave II (TDR) is still low as it is below its threshold voltage (i.e., the voltage required to change the state from "0" to "1"). According to Table 1, the "0" and "1" will result in an exclusive OR gate 80 output of 1, so the value of wave III at time A is "1." At time B, wave II (TDR) increases to the peak value so both wave I and wave II (TDR) are now "1" and wave III is now "0." The process reverses at time C when wave I becomes "0" and wave II (TDR) is still high. When wave II (TDR) drops below the threshold at time D, the output at wave III drops to "0" again. The exclusive OR gate 80 output at wave III charges capacitor 92 (FIG. 4) such that the voltage at wave IV remains nearly constant, only changing when the charge time (i.e., the time between times A and B and times C and D) increases or decreases. The charge time is directly related to the dielectric constant of the medium around the probe, which increases with high dielectrics and decreases with low dielectrics.

The FD mode functions similarly to the TDR mode. The probe now acts as a capacitor, charging when the input from wave I is high, and discharging when the input is low (FIG. 5, wave II) FD. At time A, wave I is high, while wave II (FD) begins increasing in voltage from 0. The exclusive OR gate 80 output of wave III (FD) at time A is "1." When the voltage reaches a threshold value at time B (indicated by horizontal lines on wave II (FD)), wave II changes from "0" to "1" and the output of exclusive OR gate 80 (wave III (FD)) becomes "0." Again, when wave I returns to "0," (FIG. 5, wave I), the process is reversed. The output of exclusive OR gate 80 has the same affect on the voltage at wave IV as the TDR circuitry.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention. The words "including" and "having," as used in the specification, including the claims, shall have the same meaning as the word "comprising."

What is claimed is:

1. A sensor for measuring water content of bulk materials, the sensor being powered by a direct current excitation, the sensor comprising:
    an oscillator to provide a square wave voltage signal;
    a transmission line having an input and an output, the transmission line input being coupled to receive the square wave voltage signal, the transmission line output being coupled to a phase detector;
    the phase detector detecting a phase difference between the square wave voltage signal provided by the oscillator and the signal provided to the transmission line, the phase detector providing an output signal indicative of the phase difference caused by changes in moisture content of a medium surrounding the transmission line wherein the phase detector comprises:
    a semiconductor circuit having first and second inputs and an output, the output of the semiconductor circuit being indicative of a logical exclusive OR function of signals applied to the first and second inputs of the semiconductor circuit, the first input of the semiconductor circuit being coupled to the oscillator to receive the square wave voltage signal and the second input of the semiconductor circuit being coupled to the transmission line;
    a low pass filter providing a direct current output proportional to moisture content.

2. A sensor for measuring water content of bulk materials according to claim 1 wherein a time domain reflectometry wave form is used to measure the phase difference.

3. A sensor for measuring water content of bulk materials according to claim 1 wherein a frequency domain wave form is used to measure the phase difference.

4. A sensor for measuring water content of bulk materials according to claim 1, further comprising an insulator over the transmission line.

5. A sensor for measuring water content of bulk materials according to claim 1 wherein the low pass filter comprises a resistor and a capacitor connected to the output of the semiconductor circuit producing a DC voltage proportional to the phase difference of the signals provided to the first and second inputs.

6. A sensor for measuring water content of bulk materials according to claim 1 wherein the semiconductor circuit comprises electrical traces on an elongated printed circuit board.

7. A sensor for measuring water content of bulk materials according to claim 1 wherein the semiconductor circuit comprises electrical traces on an elongated printed circuit board, and wherein the electrical traces on the elongated printed circuit board sense a dielectric constant of the bulk materials based on the measured phase difference.

8. A sensor for measuring the water content of bulk materials comprising:
    first and second elongate members, each having substantially identical shape and size so that the first and second members mate with one another and are bonded together to form a sensor;
    sensor electronics mounted on the first member, the sensor electronics being protected by a housing, the sensor electronics being responsive to a direct current excitation for providing an output signal which is proportional to an amount of water present in a bulk material;
    wherein the sensor electronics comprise:
    an oscillator responsive to a direct current excitation, to provide a square wave signal;
    a transmission line being coupled to receive the square wave voltage signal from the oscillator through a resistor, and a phase detector to detect a difference in phase between the square wave voltage signal provided by the oscillator and the signal provided to the transmission line, the phase detector being further constructed to provide an output signal indicative of the difference in phase between a square wave signal provided to the transmission line through the resistor and the response of the transmission line.

9. The sensor as recited in claim 8 wherein the output of the sensor electronics is proportional to a water content of the bulk material.

10. The sensor as recited in claim 8 wherein the phase detector comprises:
    a semiconductor circuit having first and second inputs and an output, the output of the semiconductor circuit being indicative of the phase difference of the signals applied to the first and second inputs of the semiconductor circuit, the first input of the semiconductor circuit being coupled to the oscillator to receive the square wave voltage signal and the second input of the semiconductor circuit coupled to the transmission line;
    a resistor and a capacitor providing a low pass filter connected to the output of the semiconductor circuit producing a DC voltage proportional to the phase difference of the signals provided to the inputs.

11. The sensor as recited in claim 8 where the dielectric constant of a bulk medium is sensed using a transmission line embedded in the bulk material;
    the transmission line comprising traces on an elongated printed circuit board, the circuit board further comprising a semiconductor circuit.

12. A method of measuring moisture in a bulk material, comprising: providing a transmission line comprising in input and an output; embedding the transmission line into a bulk material providing a signal to the input of the transmission line; providing a phase detector, the phase detector being operatively coupled to the output of the transmission line and a reference signal; the phase detector measuring a phase difference between the reference signal and an output signal from the transmission line to determine a moisture content of the bulk material surrounding the transmission line and further comprising: determining the dielectric constant of the bulk material by the phase difference to measure the moisture content of the bulk material.

13. A method of measuring moisture in a bulk material, comprising: providing a transmission line comprising in input and an output; embedding the transmission line into a bulk material providing a signal to the input of the transmission line; providing a phase detector, the phase detector being operatively coupled to the output of the transmission line and a reference signal; the phase detector measuring a phase difference between the reference signal and an output signal from the transmission line to determine a moisture content of the bulk material surrounding the transmission line and wherein the phase detector measures the phase difference using an Exclusive OR gate.

14. A sensor for measuring the water content of bulk materials, comprising:
- a first circuit board;
- a second circuit board bonded to the first circuit board, the first and second printed circuit boards cooperating to form a water sensor;
- sensor electronics sandwiched between the first and second circuit boards responsive to current excitation to provide an output signal indicative of an amount of water present in a bulk material, the sensor electronics further comprising:
  - a capacitor charging rate measuring circuit, comprising:
    - an oscillator to provide a wave voltage signal;
    - a transmission line sandwiched between the first and second circuit boards;
    - a capacitor electrically connected to the transmission line;
    - a phase detector electrically connected to the transmission line.

* * * * *